US00PP34967P2

(12) United States Plant Patent
Yeh

(10) Patent No.: US PP34,967 P2
(45) Date of Patent: Feb. 7, 2023

(54) ORCHID NAMED 'HONEY MICHELL'

(50) Latin Name: ***Oncidesa* Gower Ramsey**
Varietal Denomination: HONEY MICHELL

(71) Applicant: Kai-Wun Yeh, Taipei (TW)

(72) Inventor: Kai-Wun Yeh, Taipei (TW)

(73) Assignee: Kai-Wun Yeh, Taipei (TW)

( * ) Notice: Subject to any disclaimer, the term of this patent is extended or adjusted under 35 U.S.C. 154(b) by 0 days.

(21) Appl. No.: 17/803,285

(22) Filed: Apr. 20, 2022

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
See application file for complete search history.

*Primary Examiner* — Annette H Para

(74) *Attorney, Agent, or Firm* — Birch, Stewart, Kolasch & Birch, LLP

(57) ABSTRACT

A new and distinct variety of *Oncidesa* plant denominated 'HONEY MICHELL' which is with varied floral colors of white, whitish, yellow and yellowish, compared to the parent variety, i.e. HONEY ANGEL. HONEY ANGEL has yellow flowers. The height of HONEY MICHELL is about ⅔ to half to the height of the parent variety, HONEY ANGEL. Therefore, the generated new variety is suitable for the pot plant usage in the oncidium flower market. Compared to other similar dwarf oncidium hybrid orchids, which are planted and sold as ornamental pot orchids, such as *Oncidium* 'Twinkle' or *Oncidium* 'Sepia', they are only similar in plant height, around 50~70 cm height. The floret size is tiny and floret number is crowded with *Oncidium* 'Twinkle'. In contrast, the floret size of 'HONEY MICHELL' is bigger (3~5 cm width), and floret number is relatively few.

3 Drawing Sheets

Botanical classification: *Oncidesa* Gower Ramsey.
Variety denomination: 'HONEY MICHELL'.

BACKGROUND OF THE NEW VARIETY

The present invention relates to a new and distinct variety from the parent orchid, *Oncidesa* Gower Ramsey 'HONEY ANGEL'. The new variety has been given the variety denomination 'HONEY MICHELL'. This orchid's offspring is variated with different floral colors of white, whitish, yellow and yellowish, even though by using asexual propagation. The 'HONEY MICHELL' is usually dwarf, compared to its parent variety, and this new derived variety of *Oncidesa* was stable and persistent growing.

ORIGIN OF THE VARIETY

The current novel variety, i.e. 'HONEY MICHELL' is derived from the parent variety, i.e. *Oncidesa* Gower Ramsey 'Honey Angel' during the asexual tissue culture propagation process. While the *Oncidesa* Gower Ramsey 'Honey Angel' was asexually propagated by protocorm-like body (PLB) tissue culture technology, the plant hormone concentrations of culture medium were changed to higher dose, and there are few varied morphological seedlings appearing in the cultural mediums. Among the aforesaid varied seedlings, some show dwarf size and paler green leaf color after a period growth than parent seedlings. Then, such varied seedlings were isolated and grew to mature, and their flowers display white or light yellow or yellowish, and dwarf (lower height). Herewith, it is named *Oncidesa* 'HONEY MICHELL'. The tissue culture work was carried out from 2020 to 2021.

The somatoclonal variation of 'HONEY MICHELL' was caused by chemical-induced mutation, through the addition of the hormone NAA/BA at a dosage of 0.5~2.5 ppm/0.1~1 ppm to the conventional growth MS medium (½ Murashige and Skoog medium base, coconut juice 150 ml/L), MS medium contains major salts, minor salts and vitamins chemicals. Macronutrients per litre are composed of Ammonium nitrate ($NH_4NO_3$) 1650 mg/l, Calcium chloride ($CaCl_2 \cdot 2H_2O$) 440 mg/l, Magnesium sulfate ($MgSO_4 \cdot 7H_2O$) 370 mg/l, Monopotassium phosphate ($KH_2PO_4$) 170 mg/l and Potassium nitrate ($KNO_3$) 1900 mg/l. Minor salts are composed of Boric acid ($H_3BO_3$) 6.2 mg/l, Cobalt chloride ($CoCl_2 \cdot 6H_2O$) 0.025 mg/l, Ferrous sulfate ($FeSO_4 \cdot 7H_2O$) 27.8 mg/l, Manganese(II) sulfate ($MnSO_4 \cdot 4H_2O$) 22.3 mg/l, Potassium iodide (Kl) 0.83 mg/l, Sodium molybdate ($Na_2MoO_4 \cdot 2H_2O$) 0.25 mg/l, Zinc sulfate ($ZnSO_4 \cdot 7H_2O$) 8.6 mg/l, Ethylenediaminetetraacetic acid ferric sodium (Fe-NaEDTA) 36.70 mg/l and Copper sulfate ($CuSO_4 \cdot 5H_2O$) 0.025 mg/l. Vitamins and organic compounds per litre are composed of Myo-Inositol 100 mg/l, Nicotinic Acid 0.5 mg/l, Pyridoxine·HCl 0.5 mg/l, Thiamine·HCl 0.1 mg/l, Glycine 2 mg/l, Tryptone 1 g/l (optional). The generation of 'HONEY ANGEL'-derived variety, 'HONEY MICHELL', was repeated for three times at least, and the outcome is reproducible.

After protocorm-like bodies (PLB) were cultivated, propagated and shooting in the supplemented medium for 2~3 months in 8/16 hr (dark/light) at 22° C., approximately one third of the shoots appeared pale green. These shoots were selected, subcultured in fresh MS medium with the same concentration of NAA/BA as the previous medium recipe and grown up to seedlings. The mature seedlings were subsequently moved out to grow in pot and cultivated in a green house until mature plants growing-up.

The technology can generate variated progenies with different floral colors of white, whitish, yellow and yellowish, compared to the parent variety, 'HONEY ANGEL', which is bright yellow. In addition, the 'HONEY ANGEL'-derived variety plants are usually dwarf, compared to the parent variety. This new *Oncidesa* 'HONEY ANGEL'-derived variety, 'HONEY MICHELLI' is stable and persistent growing.

SUMMARY OF THE VARIETY

The new and distinct variety 'HONEY MICHELL" orchid has the following outstanding and distinguishing characteristics. The major differences between the new *Oncidesa* 'HONEY MICHELL' compared with the parent variety include characteristics of flower color, plant height and early-flowering time. The mature plant height of the new *Oncidesa* 'HONEY MICHELL' variety is about ⅔ to half of the height of the parent variety, 'Honey Angel' and other *Oncidesa* varieties. Therefore, the 'HONEY MICHELL' is suitable for the ornamental pot orchids in the oncidium flower market.

DESCRIPTION OF THE DRAWINGS

This new *Oncidesa* plant is illustrated by the accompanying photographs which show the overall plant habit including blooms, buds, and foliage of the plant; the colors shown are as true as can be reasonably obtained by conventional photographic procedures. The photographs were taken on August, 2021. Colors in the photographs may differ from the color values cited in the detailed botanical description, which accurately describe the actual colors of the new variety.

Figure 1:
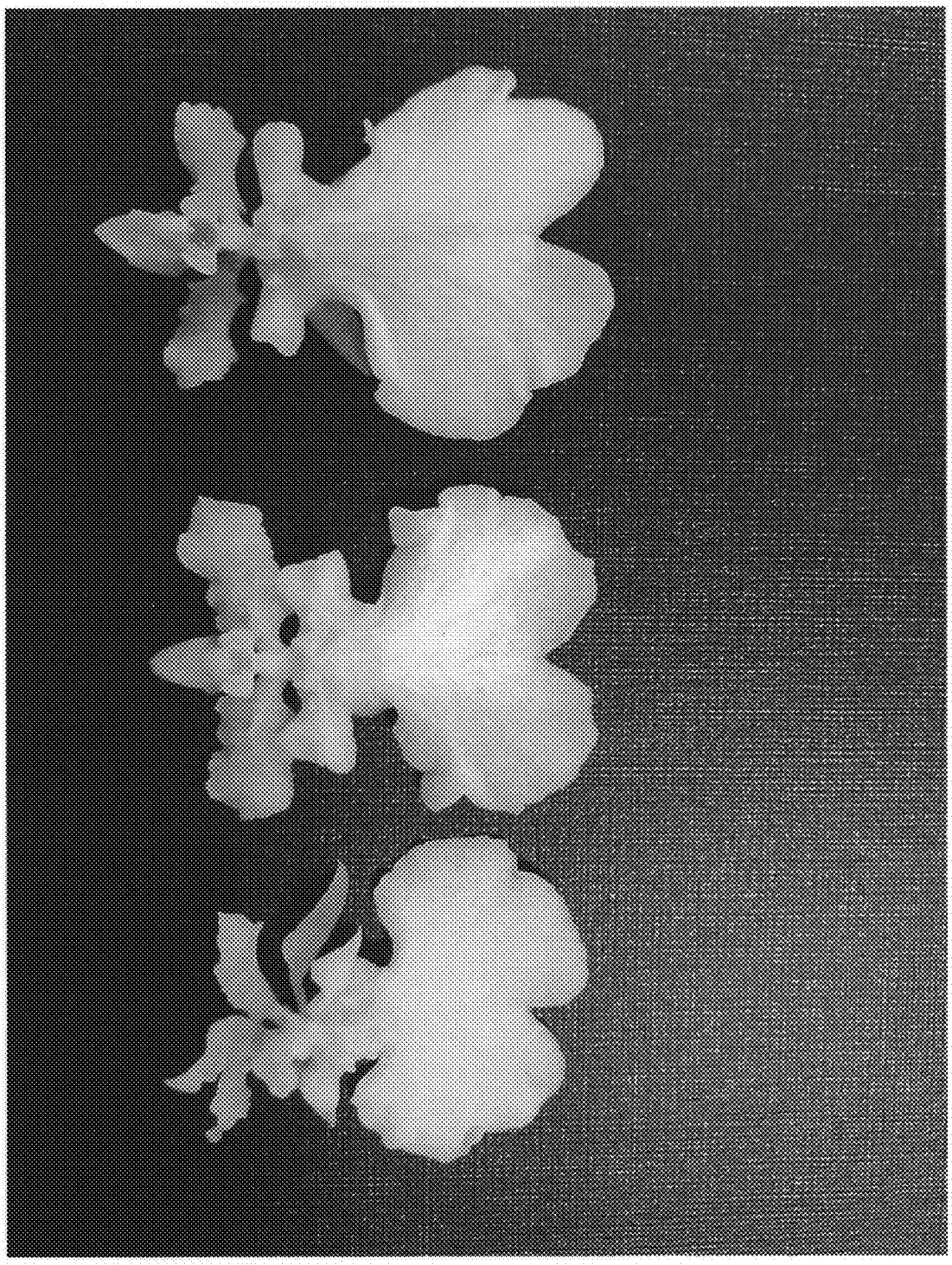
FIG. 1 and FIG. 2 show that the flower color of the *Oncidesa* 'HONEY MICHELL' is light yellow or yellowish.
Figure 2:
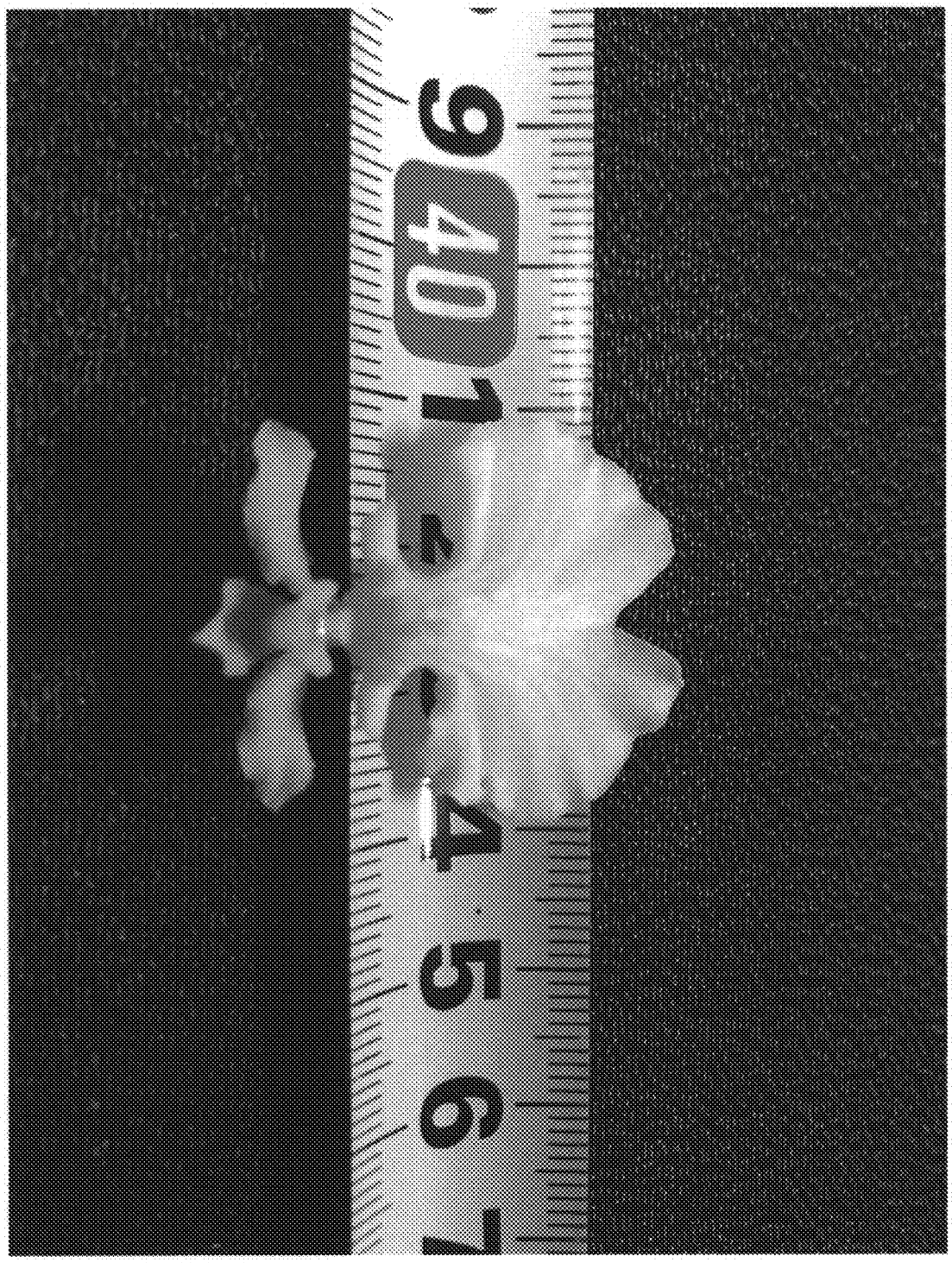
Figure 3A:
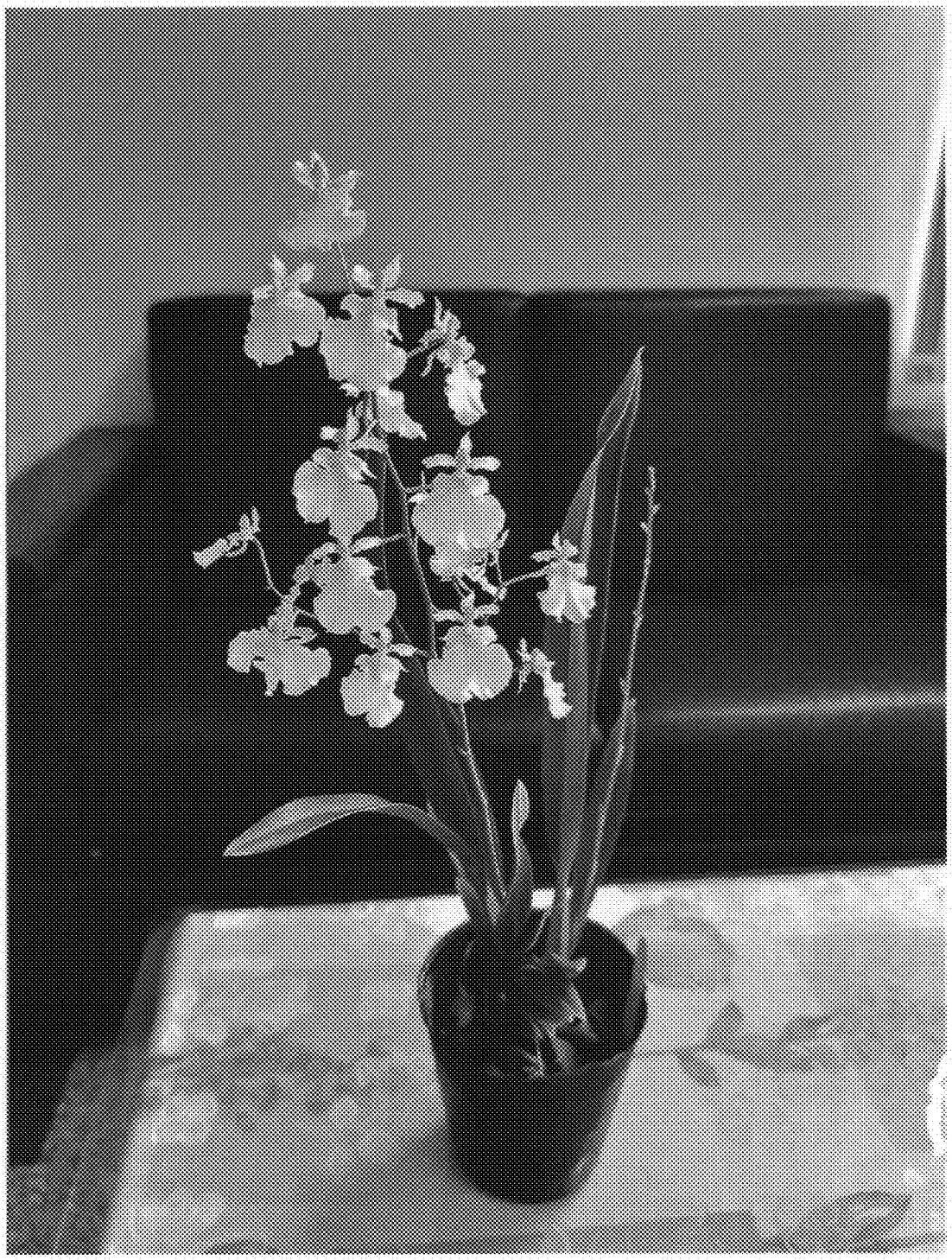
FIG. 3(A) shows the mature plant height of this *Oncidesa* 'HONEY MICHELL'.

The florescent tip of the new *Oncidesa* variety is round tip, while the florescent tip of the parent variety and other *Oncidesa* varieties are comparatively sharp.

Notes: All plants described here are cultivated in greenhouse under 16 hr days/8 hrs night, and 25° C.~32° C. Plant characters are recorded from mature plants with flowers, grown at plastic pot (~5 inch) for about 10~11 months after seedlings moved from glass flask.

DETAILED BOTANICAL DESCRIPTION (color is recorded referring to RHS mini color chart, Flower Council Holland)

Classification:

*Family.*—Orchidacaceae.

*Genus.*—*Oncidesa.*

*Common name.*—Oncidium.

*Variety name.*—'HONEY MICHELL'.

Parentage: Somatoclonal variation from PLB culture of *Oncidesa* 'HONEY ANGEL'.

Plant height and diameter: The height is about 40-50 cm and diameter: 10-15 cm.

Stem description: The stem length is 10-15 cm; diameter about 5 mm; the texture is fibrillose; the strength of the stem is tough and the stem is dark green in color (RHS141A).

Leaf description:

*Quantity of leaves per plant.*—4-10 foliar surrounding a pseudobulb The leaf shape is linear with a length about 15-40 cm and a width of about 1-3 cm; the apex is cuspidate; with the margin on the entire leaf; the texture (both surfaces) is fibrillose; the color of the leaves of upper sides is dark green RHS141A; the lower side is pale green RHS144A. The leaves are sessile.

Root description: The roots are monocot and fibrous.

Flower bud:

*Average size.*—~0.5 cm.

*Length.*—~1 cm.

*Shape.*—Almond shape.

*Color.*—Yellowish RHS8C.

Flowers:

*Flower longevity.*—On the plant: 1-2 month.

*Flower shape.*—Zygomorphic (bilateral symmetrical).

*Fragrance.*—No.

*Petals.*—Arrangement: Contorted aestivation. Shape: oblong. Margin: wave. Color: white RHS155A to yellow RHS6A.

*Dorsal sepal.*—Shape: parallel. Apex: sharp tip. Margin: wave. Color: white RHS155B to yellow yellow RHS12A and RHS6A.

*Lateral sepals.*—Shape: parallel. Apex: sharp tip. Margin: wave. Color: white RHS155B to yellow RHS 7D.

*Labelleum.*—Whiskers absent. Color: white RHS155B to yellow RHS12A and RHS6A.

*Lateral lobe.*—Shape: reniform. Color white RHS155B to yellow yellow RHS 7D.

*Apical lobe.*—Shape: absent. Color: absent.

*Callus.*—Average size: 2 mm. Height: 1~2 mm. Length: 1~2 mm. Width: 3~4 mm. Color: yellow RHS 13B.

Reproductive organs:

*Column.*—Length: 2-5 mm. Diameter: 1-3 mm. Color: yellow RHS13B.

*Pollinia.*—Quantity: 2. Diameter:0.2-0.5 mm. Color: yellow, RHS7D.

*Ovary.*—Length: 1-3 mm. Diameter: 0.5 mm.

*Pedicel.*—Length: 2-5 cm. Diameter: 2-5 mm. Color: green RHS139C. Texture: fibrillose. The flowers have a height of about 25 cm; diameter of about 2-3 cm; the plant blooms when the pseudobulb is mature with 30-80 florets/per stem; the color of the flowers is white (RHS 157B) to yellowish (RHS7D) or yellow (RHS 12A).

Rostellum: The rostellum forms a column type with a length of about 0.2-0.5 cm; a thickness of about 0.1-0.3 cm and a color of pale yellow RHS 13B.

I claim:

1. A new and distinct variety of *Oncidesa* name HONEY MICHELL as illustrated and described, characterized herein.

* * * * *